United States Patent
Hughes et al.

(10) Patent No.: US 9,424,393 B2
(45) Date of Patent: *Aug. 23, 2016

(54) METHOD, APPARATUS, AND SYSTEM FOR READING, PROCESSING, PRESENTING, AND/OR STORING ELECTRONIC MEDICAL RECORD INFORMATION

(71) Applicant: EMERGENT HEALTH CARE SOLUTIONS, LLC, Springfield, OR (US)

(72) Inventors: Rexford Irving Hughes, Springfield, OR (US); Daniel Charles Fitzpatrick, Eugene, OR (US); William Dale Denny, Springfield, OR (US); Cale Gage Bruckner, Eugene, OR (US); Charles Martel Augustine, Eugene, OR (US); Jason Lloyd Cowsill, Eugene, OR (US); Howard Wayne Skipper, Eugene, OR (US)

(73) Assignee: EMERGENT HEALTH CARE SOLUTIONS, LLC, Springfield, OR (US)

( * ) Notice: Subject to any disclaimer, the term of this patent is extended or adjusted under 35 U.S.C. 154(b) by 253 days.

This patent is subject to a terminal disclaimer.

(21) Appl. No.: 14/307,042

(22) Filed: Jun. 17, 2014

(65) Prior Publication Data

US 2014/0304005 A1    Oct. 9, 2014

Related U.S. Application Data

(63) Continuation-in-part of application No. 13/188,164, filed on Jul. 21, 2011, now Pat. No. 8,775,213.

(51) Int. Cl.
| | |
|---|---|
| *G06Q 50/22* | (2012.01) |
| *G06Q 50/24* | (2012.01) |
| *G06F 19/00* | (2011.01) |
| *G06F 3/041* | (2006.01) |
| *G06Q 10/10* | (2012.01) |

(52) U.S. Cl.
CPC ............ *G06F 19/322* (2013.01); *G06F 3/041* (2013.01); *G06F 19/3406* (2013.01); *G06Q 10/10* (2013.01); *G06Q 50/22* (2013.01)

(58) Field of Classification Search
CPC .... G06Q 50/22; G06Q 50/24; G06F 19/321; G06F 19/322
See application file for complete search history.

(56) References Cited

U.S. PATENT DOCUMENTS

| | | | |
|---|---|---|---|
| 7,225,131 B1 | 5/2007 | Bangalore et al. | |
| 7,621,445 B2 | 11/2009 | Esseiva et al. | |
| 7,966,578 B2 | 6/2011 | Tolmasky et al. | |
| 2009/0024417 A1* | 1/2009 | Marks | G06F 19/322 705/3 |
| 2010/0131294 A1* | 5/2010 | Venon | G06F 19/321 705/3 |

* cited by examiner

*Primary Examiner* — Joseph Burgess
(74) *Attorney, Agent, or Firm* — David A. Crowther

(57) ABSTRACT

A method for accessing, processing, presenting, and/or storing electronic medical record (EMR) information on a touch-sensitive display includes reading EMR information, displaying at least a portion of the EMR information on a touch-sensitive sliding timeline, detecting finger swipe or similar gestures, and scrolling the sliding timeline so that a different portion of the EMR information is displayed chronologically on the touch-sensitive sliding timeline. The resolution of the timeline can be expanded or collapsed in response to pinch gestures. The timeline is divided into a columns, each column including icons representing medical related events. A second timeline having a different time resolution from the first timeline is used for navigating the medical related events. Different levels of detail regarding the medical related events can be viewed in different detail panes. An EMR access device and system are also disclosed, which are configured to access and present EMR information.

20 Claims, 10 Drawing Sheets

FIG. 6

EMR ACCESS USER INTERFACE 115

DONE 605

SECOND AND/OR THIRD LEVEL DETAIL PANE 690

FIG. 8

EMR ACCESS USER INTERFACE 115

| CANCEL 802 | SCRIBBLE PAD 800 | SAVE 804 |

Knee —806    808— R / L

HPI onset    (days)   weeks   months   ←810
         ←810 context   fall   twist   impact
                              ←810 severity   mild ———————/—— severe
                              ←810 quality    achey   dull   sharp   throbbing   burning instability   catching   locking   swelling

EXAM

Effusion  —  ←810

Lachman's +         380

397

Pivot Shift +

Anterior Drawer —         810    0
                                  30
Posterior Drawer —  120  /90  60              812

814

PLAN

MRI    Relafen    Celebrex    Anthroscopy
  ←810
PT     Naprosyn   Synvisc     ACL reconst     818

| DRAWING TOOLS 816 | ▬▬▬●——— |

←820

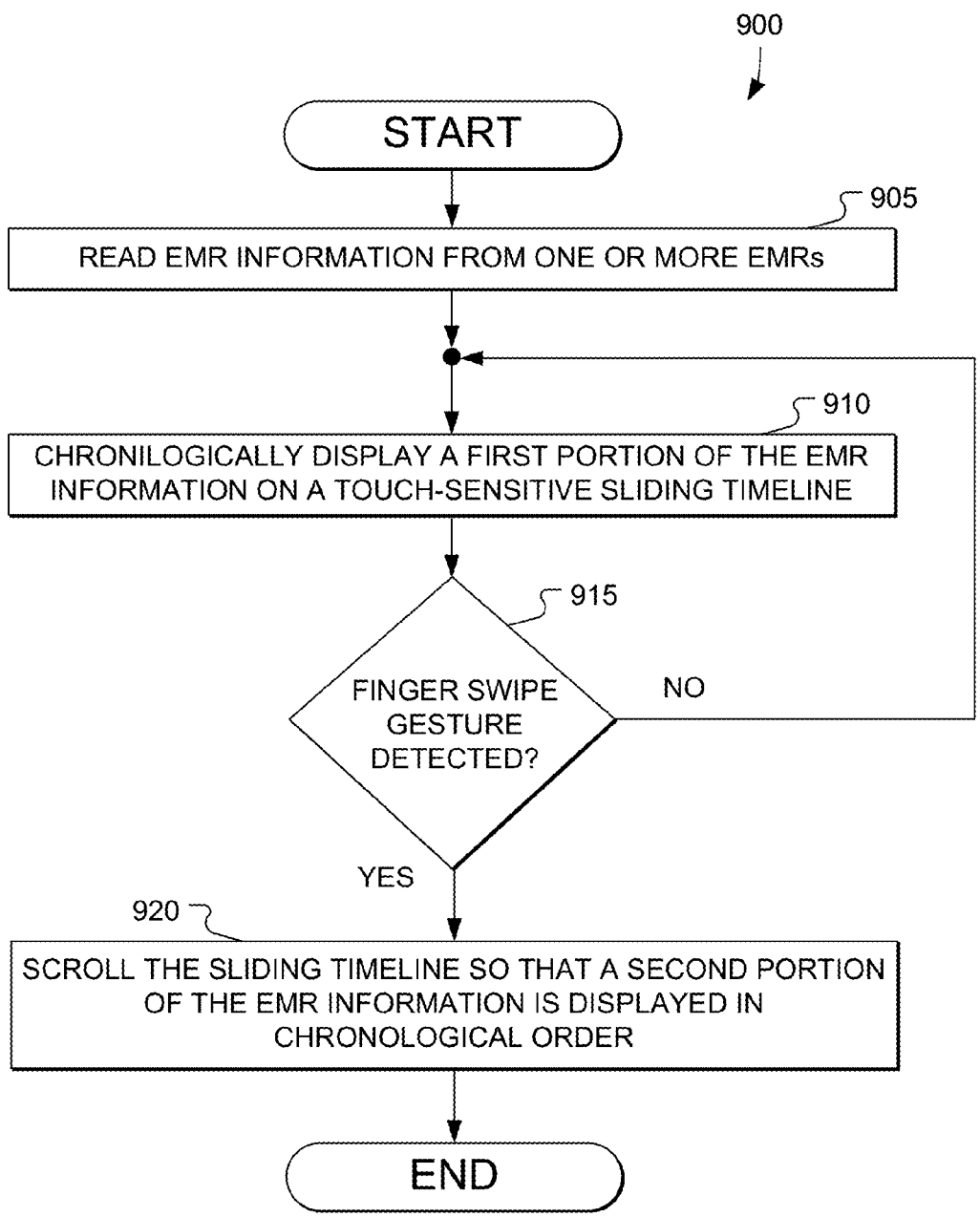

METHOD, APPARATUS, AND SYSTEM FOR READING, PROCESSING, PRESENTING, AND/OR STORING ELECTRONIC MEDICAL RECORD INFORMATION

RELATED APPLICATION DATA

This application is a continuation-in-part of and claims priority from commonly assigned U.S. patent application Ser. No. 13/188,164, filed Jul. 21, 2011, which is hereby incorporated by reference in its entirety.

TECHNICAL FIELD

This disclosure relates to electronic medical records, and, more particularly, to a method, apparatus, and system for reading, processing, presenting, and storing electronic medical record information on a touch-sensitive display device.

BACKGROUND

Effective interactions between doctors and patients are crucial to establishing a relationship of trust. In today's highly technical world, vast amounts of medical information are stored in large computerized databases. Typically, such databases store the medical information about patients as electronic medical records, generally referred to as EMRs. Such EMRs contain various information about patients such as their medical history, allergies, medications, diagnostic information, test results, among myriad other types of medical events and information. EMRs have become an integral part of the evolution from paper medical records to electronically stored medical records.

Conventional interfaces with EMR databases are somewhat proficient at receiving information about the patient, categorizing such information, and storing such information in the database. However, due to the massive amounts of information stored in the database, and the inability to quickly access and use such information without using a complex interface, it is difficult or impossible for doctors to efficiently communicate with patients, particularly when the patient is present in the office and the conversation is occurring in "real-time."

As patients become more Internet savvy and pursue medical information in advance of conversations with their doctor, the desire to communicate with their doctor at a heightened level of detail is becoming ever more acute. Whereas in times past, the patient might be content with the simple assurance of their doctor that things will just be okay, now the patient might demand instant information about a test result, the prognosis after a medical procedure, the possible reactions to a medication, a meticulous explanation of what to expect during a surgery, and so forth.

But reading and presenting EMR information is tedious for doctors, and virtually impossible for patients. Entry of information and access to the EMR information is usually done through a generalized computer, through a complex web of menus and entry fields. Very little about the traditional interfaces makes life easy for the doctor-patient relationship. Indeed, the conventional technology in some ways throws up barriers to this relationship because of communication delays caused by the inability to quickly and conveniently share medical information with the patient.

If a doctor wants to share a medical picture or record about the patient, the patient must wait for the doctor to wade through the EMR information using a computer keyboard and a mouse until the sought out information is located, and thereafter, attempt to explain the significance of the information even though there might be different unrelated data showing in the same window, thereby obscuring the pertinent information and lessoning the quality and effectiveness of the doctor-patient interaction. Entering and storing information is equally as difficult, and requires significant time and training so that the information is entered and stored without introducing inaccuracies into the database.

These are only a few of the challenges presented by conventional approaches, which are impeding the wider adoption of electronically stored medical data. Efficiencies associated with the convergence of medical record information and information technology advances are therefore not realized in many situations. The costs associated with medical care will continue to rise at a pace that would otherwise be unnecessary if greater efficiencies were brought to bear.

Accordingly, a need remains for an improved method, apparatus, and system for reading, processing, presenting, and storing electronic medical record information. In addition, a need remains for improving the interactions between patients and their doctors. Embodiments of the invention address these and other limitations in the prior art.

BRIEF DESCRIPTION OF THE DRAWINGS

FIG. 6 illustrates the touch-sensitive user interface in still another example mode for accessing and presenting EMR information according to some embodiments of the present invention.

FIG. 8 illustrates the touch-sensitive user interface in another example mode for accessing and presenting EMR information according to some embodiments of the present invention.

FIG. 9 illustrates a flow diagram including techniques for reading and displaying EMR information in a touch-sensitive sliding timeline, according to example embodiments of the invention.

The foregoing and other features of the invention will become more readily apparent from the following detailed description, which proceeds with reference to the accompanying drawings.

DETAILED DESCRIPTION

Reference will now be made in detail to embodiments of the invention, examples of which are illustrated in the accompanying drawings. In the following detailed description, numerous specific details are set forth to enable a thorough understanding of the present invention. It should be understood, however, that persons having ordinary skill in the art may practice the present invention without these specific details. In other instances, well-known methods, procedures, components, circuits, and networks have not been described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first gesture could be termed a second gesture, and, similarly, a second gesture could be termed a first gesture, without departing from the scope of the present invention.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of a portable EMR access apparatus, user interfaces for such apparatus, associated methods and processes for using such apparatus, and associated systems with which such apparatus can be used, are described. In some embodiments, the device is a portable communications device having a touch-sensitive display, sometimes referred to as touch screen. Such portable touch-sensitive device can be a mobile tablet computer, a mobile telephone having a touch-sensitive screen, a personal digital assistant (PDA) having a touch-sensitive screen, or the like. The touch-sensitive display can receive touch signals from a human finger, thumb, or the like, and/or by using a stylus.

Figure 1:
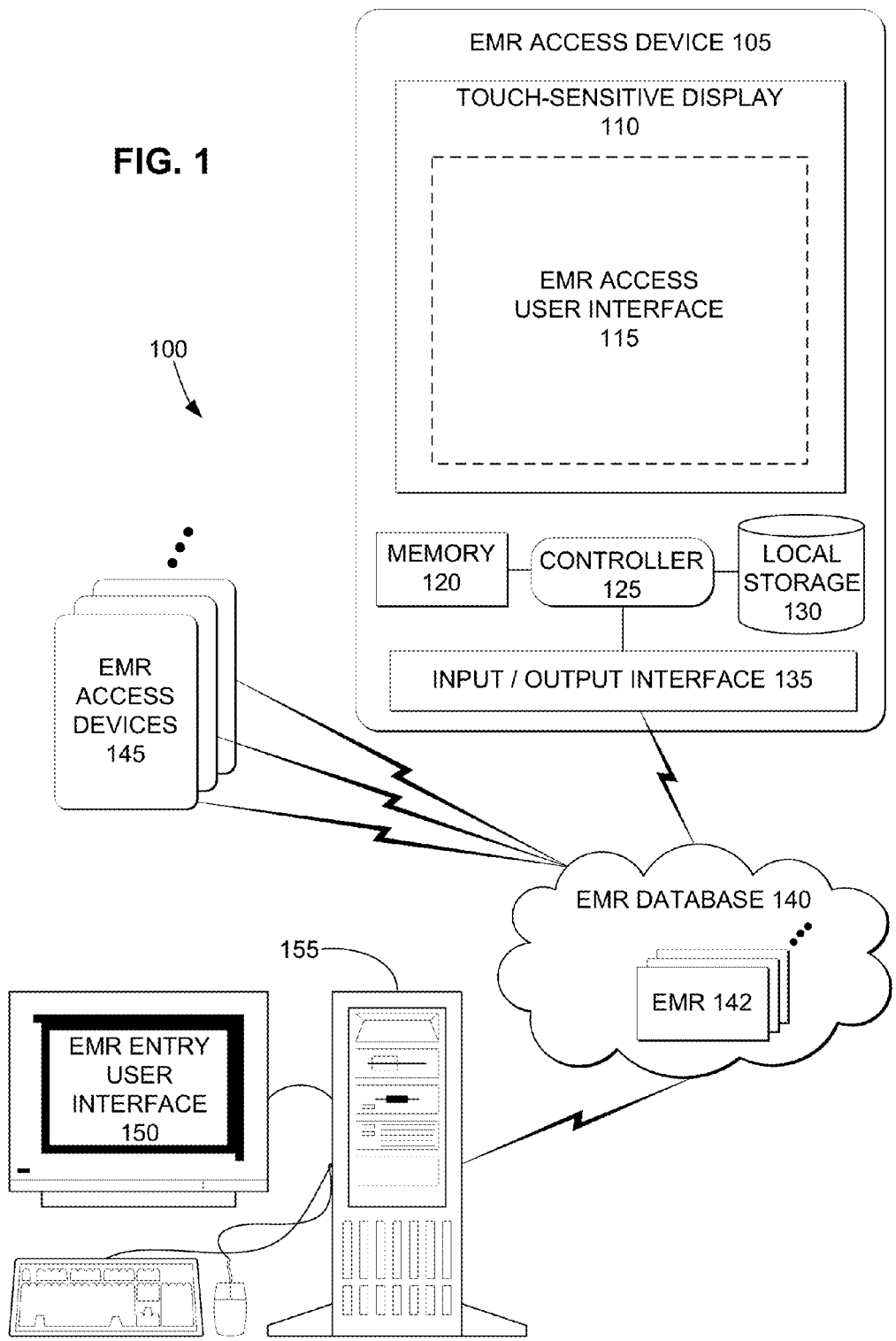
FIG. 1 illustrates a system including an electronic medical record (EMR) database and one or more EMR access devices according to an example embodiment of the present invention.

FIG. 1 illustrates a system 100 including an electronic medical record (EMR) database 140 and one or more EMR access devices (e.g., 105, 145) according to an example embodiment of the present invention.

The EMR database 140 stores electronic medical information including EMRs 142. The EMR database 140 can be populated using an EMR entry user interface 150, which can operate on a general purpose personal computer 155.

One or more portable EMR access devices (e.g., 105, 145) can be configured to access or otherwise communicate with the EMR database 140. The EMR access devices can extract EMR information 142 from the EMR database 140 and/or transmit EMR information 142 to the EMR database 140 for storage. The EMR access device can include an input output interface 135. The input output interface 135 can be configured to wirelessly communicate with a device associated with the EMR database 140, or alternatively, it can communicate with the EMR database 140 through a wired connection.

A local storage device such as a disk 130 and/or a memory 120 can be controlled by a controller 135 of the EMR access device so that the EMR information 142 received from the EMR database 140 can be stored, or other medical record information produced by the EMR device (e.g., 105, 145) can be stored. The memory 120 can be any variety of memory. For example, the memory 120 can be dynamic memory, static memory, read-only memory, random-access memory, or the like. The disk 130 can be any variety of magnetic hard drive, optical disc, flash drive, or the like.

The controller 125 is configured to process the EMR information 142, and also control components of the EMR access device 105, such as a touch-sensitive display or screen 110. The touch-sensitive display or screen 110 is configured to display the EMR information in an intuitive and convenient fashion, as described in detail below. The touch-sensitive display 110 can receive touch selections from a human finger, for example, for efficient selection and presentation of EMR information on the display 110, as also further described in detail below.

The one or more EMR access devices (e.g., 105, 145) include a user interface 115 associated with the touch-sensitive display 110. The user interface 115 includes various touch-sensitive sliding timelines, informative icons, organized lists, detail panels, and so forth, to facilitate the access and presentation of EMR information to doctors and patients.

Figure 2:
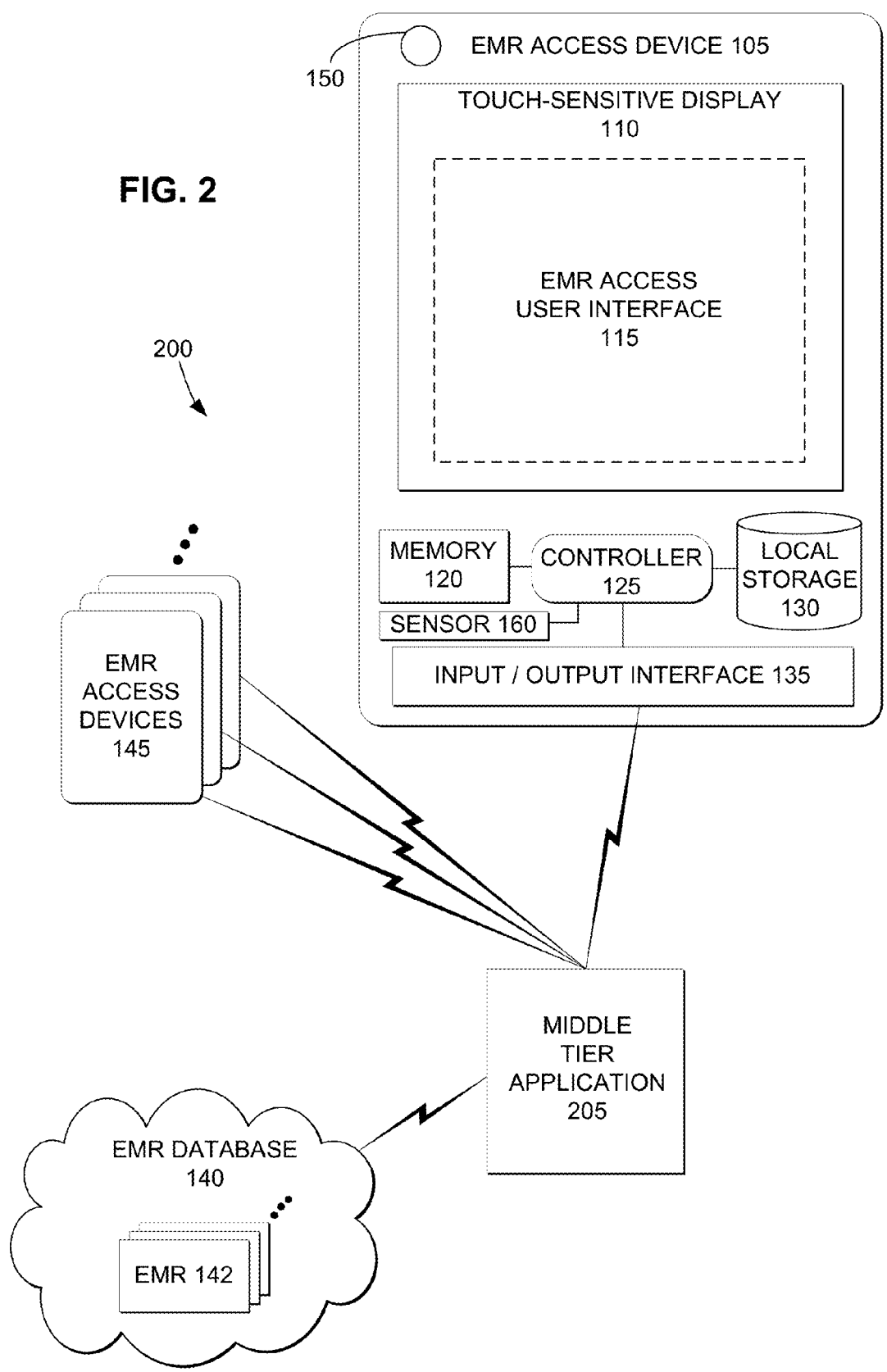
FIG. 2 illustrates a system including an electronic medical record (EMR) database, a middle-tier application, and one or more EMR access devices according to another example embodiment of the present invention.

FIG. 2 illustrates a system 200 including the electronic medical record (EMR) database 140, a middle-tier application 205, and one or more EMR access devices (e.g., 105, 145) according to another example embodiment of the present invention. Rather than communicate directly with the EMR database 140, the one or more EMR access devices can communicate with the middle-tier application 205, which communicates with the EMR database 140.

In other words, the EMR access devices can extract EMR information 142 from the middle-tier application 205 and/or transmit EMR information 142 to the middle-tier application 205 for storage. As mentioned above, the EMR access device can include an input output interface 135. The input output interface 135 can be configured to wirelessly communicate with a device associated with the middle-tier application 205, or alternatively, it can communicate with the middle-tier application 205 through a wired connection.

The middle-tier application 205 is configured to map and/or translate the information stored in the EMR database 140 into a format that is displayable by the EMR access device. In some embodiments, the middle-tier application 205 is configured to cache some or all of the EMRs 142 from the EMR database 140, or portions of such EMRs 142, which decreases the response time experienced by the EMR access devices when accessing EMR information. In addition, the middle-tier application 205 is configured to temporarily and/or permanently store information received from the EMR access devices, and periodically flush the stored EMR information to the EMR database 140. Moreover, the middle-tier application 140 can re-organize the EMRs 142, or portions thereof, into a format that is more easily accessible by the EMR access devices (e.g., 105, 145). For instance, only information that is deemed to be most pertinent or most-often-accessed, can be stored by the middle-tier application 205. In this fashion, overall performance of the system is enhanced.

The one or more EMR access devices (e.g., 105, 145) may each include a camera 150. The camera 150 can capture a photograph of a patient body part (such as a knee, an abdomen, a face, etc.). The one or more EMR access devices can cause the photograph to be stored in the EMR database 140. In addition, the EMR access devices can include a sensor 160 coupled to the controller 125. The sensor 160 can remotely sense and/or identify a particular patient within a vicinity of a healthcare facility, or within a particular predefined vicinity or distance to a particular EMR access device. Upon sensing the presence of the particular patient, medical records for the particular patient can be automatically opened and displayed on the EMR access device 105. The sensor 160 can sense, for example, a unique signature or other identifier broadcast by a patient's mobile phone. In this manner, the EMR access device 105 can efficiently access and display the appropriate medical records with little to know human action.

Other elements of the system 200 are described with reference to the system 100 above, and therefore for the sake of brevity, a detailed description of these elements is not repeated.

Figure 3:
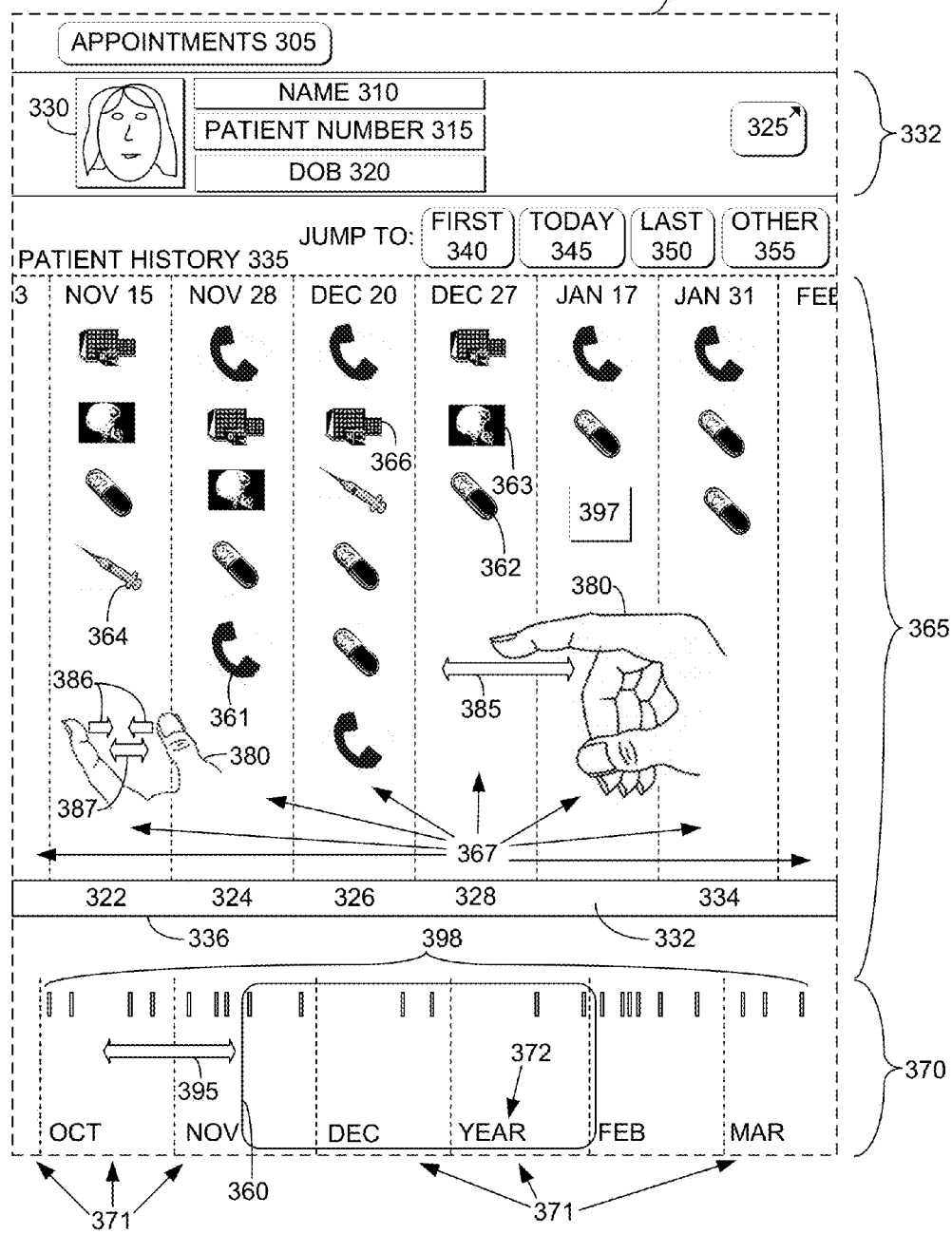
FIG. 3 illustrates a touch-sensitive user interface in one example mode for accessing and presenting EMR information according to some embodiments of the present invention.

FIG. 3 illustrates a touch-sensitive user interface 115 in one example mode for accessing and presenting EMR information according to some embodiments of the present invention.

The user interface 115 includes a patient information section 332, preferably toward the upper area of the interface, which can include basic information about the patient such as an image of the patient 330, the patient's name 310, an identification number 315 for the patient, the patient's date of birth 320, among other suitable patient information. An expansion button or icon 325 can be located in the patient information section 332, which when touched by a user of the EMR access device, expands the patient information section 332 into a patient demographics detail screen, as further described below. An appointments indicator 305 can be located above the patient information section 332, that when touched by a user, causes the EMR access device to show a list of appointments associated with the patient (not shown).

To provide "at your fingertips" access to the EMR information, the user interface 115 includes a patient history section 335. The patient history section 335 includes a first sliding timeline 365 in which a portion of the EMR information is displayed in chronological order in a group of columns 367, each column corresponding to one calendar day or one calendar week.

The EMR access device can be configured to scroll the first sliding timeline after detecting a finger swipe gesture 385 on the touch-sensitive display 110 by the user's finger 380, or other extremity such as a thumb or stylus. Although the term "finger swipe" is used herein, it should be understood that such term can encompass a swipe gesture using a stylus or other tool.

The EMR access device displays a first portion of the EMR information in chronological order on the touch-sensitive sliding timeline 365, and after detecting the finger swipe gesture 385 on or about the sliding timeline 365, the EMR access device scrolls or otherwise changes the contents of the sliding timeline so that a second portion of the EMR information is displayed in chronological order on the touch-sensitive sliding timeline 365.

It should be understood that the finger swipe gesture 385 can be in any direction, and the EMR access device can be configured to detect the intended scrolling direction of the user, and cause the sliding timeline to scroll in the intended direction. The direction of scrolling is preferably in a horizontal direction as shown in FIG. 3, although it should be understood that the direction can also be vertical, diagonal, or the like.

The EMR access device can also be configured to detect an inward finger pinch gesture 386 on the touch-sensitive display on or near the sliding timeline 365 by the user's fingers 380. It should be understood that the term "fingers" as used herein can include thumbs, etc. After detecting such an inward gesture, the resolution of the sliding timeline 365 can be expanded from increments of days 367 to increments of weeks 367. Conversely, the EMR access device can detect an outward finger pinch gesture 387 on the touch-sensitive display on or near the sliding timeline 365. After detecting such an outward gesture, the resolution of the sliding timeline 365 can be collapsed from increments of weeks 367 to increments of days 367.

The patient history information 335 is divided into columns 367. Each column is correlated with one calendar day or one calendar week. The correlated columns of patient history information can be horizontally scrolled after detecting the finger swipe gesture 385.

One or more icons (e.g., 361, 362, 363, 364, 366), can be displayed in one or more of the columns 367. Each of the icons can represent a medical event or the like. Each icon can correspond to or otherwise represent the medical event, which occurred on the given day or week associated with the day or week column, respectively, in which the icon is located.

For example, a telephone call icon (e.g., 361) can represent a telephone call placed by the doctor, patient, nurse, or hospital. As another example, an office visit icon (e.g., 366) can represent a visit by the patient to the medical office, hospital, and so forth. An oral medication icon (e.g., 362) can represent an oral medication related event, such as a prescription given by the doctor to the patient for a particular medication. Moreover, an intravenous or injection icon (e.g., 364) can represent an intravenous or injection medication related event such as a shot given to the patient. Similarly, a medical diagnostics icon (e.g., 363) can represent a medical diagnostics related event such as an x-ray, CT scan, MRI, or the like. The icons can be listed from top to bottom within a column in the order in which the associated medical events occurred.

These are but a few examples of the types of icons that can represent medical related events. It should be understood that other types of icons or graphics can be used to represent the aforementioned medical related events. It will also be understood that other types of icons or graphics can be used to represent different kinds of medical related events besides those expressly mentioned herein.

The EMR access device can detect a touch selection of an icon (e.g., 361, 362, 363, 364, 366), and then cause information about the medical related event to appear in a detail pane, as further described below.

The patient history section 335 further includes a second sliding timeline 370 proximate to the first sliding timeline 365. The second sliding timeline 370 is divided into a group of columns 371. Each of the columns 371 is correlated with one calendar month. At the beginning of a calendar year, a year indicator 372 can be displayed within the calendar month column corresponding to January.

The EMR access device can be configured to scroll the second sliding timeline 370 after detecting a finger swipe gesture 395 on the touch-sensitive display 110, preferably within the boundaries of the second sliding timeline 370. The boundaries of the second sliding timeline 370 define outer edges of the monthly columns 371.

It should be understood that the finger swipe gesture 395 can be in any direction, and the EMR access device can detect the intended scrolling direction of the user, and cause the sliding timeline 370 to scroll in the intended direction. The direction of scrolling is preferably in a horizontal direction as shown in FIG. 3, although it should be understood that the direction can also be vertical, diagonal, or the like.

The EMR access device can be configured to automatically scroll the first sliding timeline 365 to correlate in time with the second sliding timeline 370 after detecting the finger swipe gesture 395 relative to the second sliding timeline. Similarly, the EMR access device can be configured to automatically scroll the second sliding timeline 370 to correlate in time with the first sliding timeline 365 after detecting the finger swipe gesture 385 relative to the first sliding timeline.

One or more icons 398 can be displayed on the second sliding timeline 370 representing a day within at least one of the calendar months in which a medical event occurred. In other words, the icons 398 indicate that there is an event on that particular day within each of the month columns 371. The icons 398 are spaced within each month column according to the relative position of the day within the month on which the event occurred. This allows the user to know that there are events not on the first timeline, which can then be easily scrolled to.

The second sliding timeline 370 can include a shadow window 360, which correlates to the amount of time showing in the first sliding timeline 365. In other words, the shadow window 360 informs the user of the location of the first sliding timeline 365 within the context of the second sliding timeline 370. Put differently, the window 360 "shadows" the first sliding timeline 365 relative to the second sliding timeline 370. The icons 398 that appear within the shadow window 360 correlate with medical related events indicated by icons (e.g., 361, 362, 363, 364, 366) that appear in the first sliding timeline 365. In this manner, events that appear in both the first and second sliding timelines can quickly be understood in the context of time, on both wide (e.g., 370) and narrow (e.g., 365) scopes simultaneously.

The EMR access device can be configured to automatically scroll the first sliding timeline 365 to directly correlate in time with the shadow window 360 of the second sliding timeline 370 after detecting the finger swipe gesture 395 in the second sliding timeline. Similarly, the EMR access device can be configured to automatically scroll the second sliding timeline 370 so that the shadow window 360 directly correlates in time with the first sliding timeline 365 after detecting the finger swipe gesture 385 in the first sliding timeline.

The EMR access device can be configured to detect certain touch selections to jump to particular areas within a timeline. For example, the EMR access device can be configured to detect a touch selection of a "first" event preference 340 on the touch-sensitive display 110. In response to such selection, the EMR access device can automatically scroll the first sliding timeline 365 to the first calendar day column associated with the patient history information 335. In addition, the second sliding timeline 370 can be scrolled to the first calendar month associated with the patient history information 335.

Similarly, the EMR access device can be configured to detect a touch selection of a "last" event preference 350 on the touch-sensitive display 110. In response to such selection, the EMR access device can automatically scroll the sliding timeline 365 to the last calendar day column associated with the patient history information 335. In addition, the second sliding timeline 370 can be scrolled to the last calendar month associated with the patient history information 335.

Moreover, the EMR access device can be configured to detect a touch selection of a "today" event preference 345 on the touch-sensitive display 110. In response to such selection, the EMR access device can automatically scroll the sliding timeline 365 to the calendar day column corresponding to the present calendar day associated with the patient history information 335. In addition, the second sliding timeline 370 can be scrolled to the present calendar month associated with the patient history information 335. An "other" event preference 355 can indicate some other customizable location to which the timeline can jump.

A photograph of the patient 330 can be displayed for easy and efficient identification. The photograph of the patient 330 can be obtained using the camera 150 of the EMR access device 105 (of FIGS. 1 and 2). A photograph 397 of a body part of the patient 330 can be displayed on the sliding timeline 365. The photograph 397 can be selected and a larger version of the photograph can be displayed.

Medical test results in a test results section 336 can be displayed adjacent to or proximate to the sliding timeline 365. For example, a test result 322 can be displayed below a particular day (e.g., NOV. 15) of the sliding timeline. Other test results (e.g., 324, 326, 328, and 334) can be displayed in connection with other times or days associated with the sliding timeline 365. Test results need not be included for every time or day. In other words, a blank 332 or other suitable indicator can appear if there are no test results to display. The user can see the correlation of the test results at a given time relative to other events and/or medical event indicators in the timeline. For example, a historical graph of the patient's blood pressure and/or complete blood count (CBC) results can be displayed below the timeline 365. In addition, the date of each data point can be correlated with the timeline date so that the test results are aligned with historical events. The user (e.g., doctor, physician, surgeon, nurse, or other health care provider, etc.) can determine that a medication was given on a certain date and perceive how the medication affected the patient's test results 336. The physician or health care provider can then make any necessary adjustments to the medication based on the historical correlated record of events and test results. The test results section 336 may occupy any suitable portion of the touch-sensitive display 110.

Figure 4:
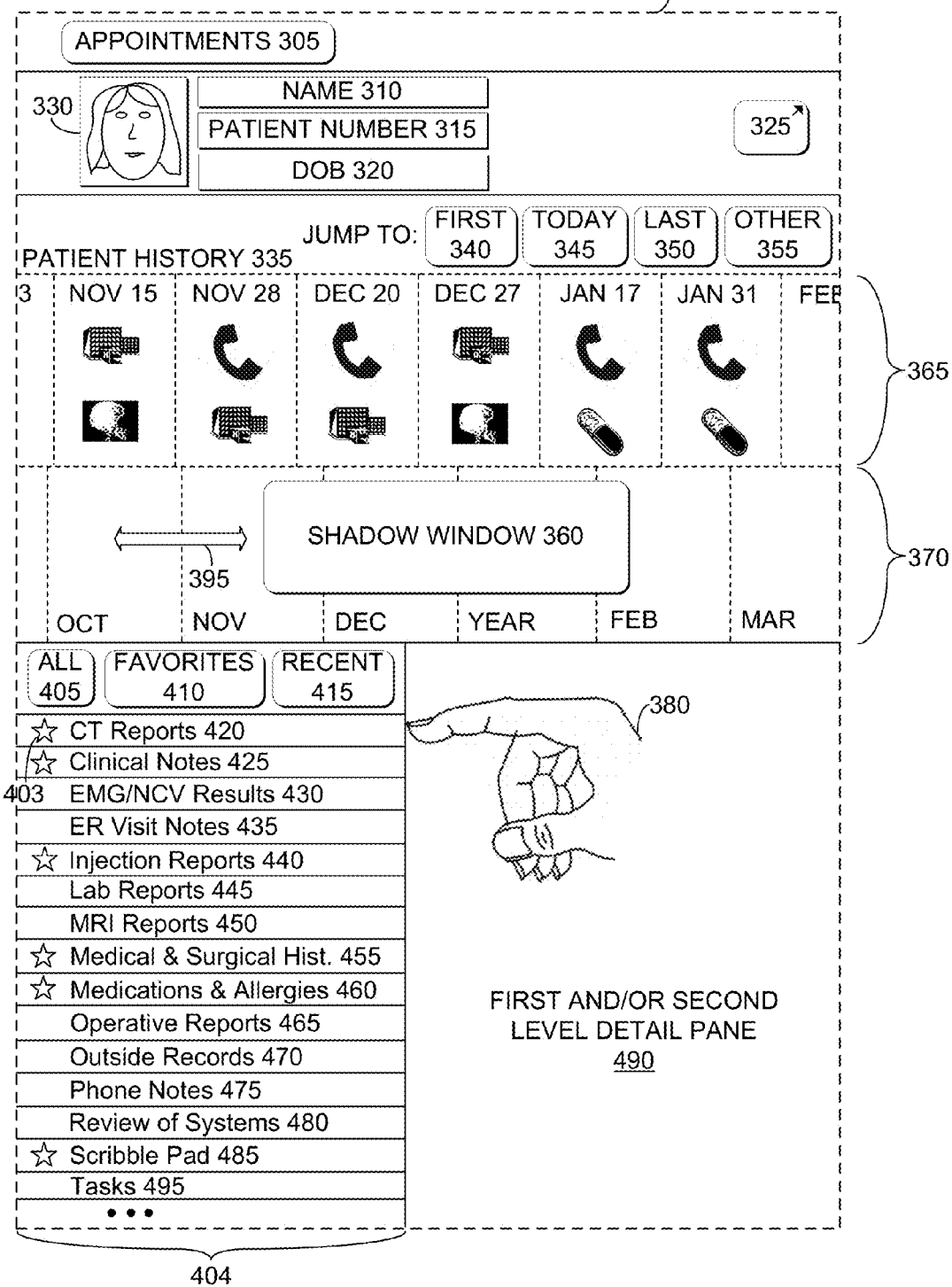
FIG. 4 illustrates the touch-sensitive user interface in another example mode for accessing and presenting EMR information according to some embodiments of the present invention.

FIG. 4 illustrates the touch-sensitive user interface 115 in another example mode for accessing and presenting EMR information according to some embodiments of the present invention. Here, the first timeline 365 is condensed so that only some of the icons (e.g., 361, 362, 363, 364, 366) are shown. The first timeline 365 can still be used in this mode, and can be scrolled either horizontally to change the time resolution, or vertically to change which icons are shown within the columns. The second sliding timeline 370 is located proximate to the first sliding timeline 365. Details of the first and second sliding timelines are provided above and for the sake of brevity are not repeated.

A list of medical categories 404 is displayed, which is associated with the medical patient 330. The list 404 can include, for example, CT reports 420, clinical notes 425, electromyogram and/or nerve condition velocity (EMG/NCV) results 430, emergency room (ER) visit notes 435, injection reports 440, lab reports 445, magnetic resonance imaging (MRI) reports 450, medical and/or surgical history information 455, medication and/or allergy information 460, operative reports 465, outside records 470, phone notes 475, review of systems 480, and/or scribble pad 485, tasks 495, among any other pertinent medical information, or any combination thereof. The order in which the categories are listed is exemplary and it should be understood that these can be in any suitable order including alphabetical, numerical, or by some other sorted preference.

Each item in the list 404 corresponds to a category of medical information associated with the medical patient. The user can select a group of "favorite" categories from the list so that only a subset of the categories appear in the list 404. For instance, the EMR access device can be configured to detect a touch selection of one of the categories in the subset of categories 410 corresponding to one category of medical information. A star indicator 403 can indicate that the category has been selected as one of the "favorite" categories. This can be repeated for other categories in the list desired to be favorites. It should be understood that the star graphic is but one example, and other types of graphics can be used to indicate the favorite categories.

The user (e.g., doctor, physician, surgeon, nurse, or other health care provider, etc.) of the EMR access device 105 can electronically mark a particular record as having been reviewed. For example, the CT reports 420, the injection reports 440, the lab reports 445, the MRI reports 450, the operative reports 465, and the like, can be accessed and reviewed, and marked as such. The marking can be made using a button on the touch-sensitive display 110. Alternatively or in addition, the marking can be made by adding an electronic signature to the particular record or report. The electronic signature can be made using the touch-sensitive display 110. The signed record or report can be transmitted to the middle-tier application 205 and/or to the EMR database 140 and stored for later retrieval. Alternatively or in addition, a flag can be stored in the database indicating that a particular record was reviewed and/or signed. Thus the user is able to sign off on or otherwise approve patient records using the EMR access device 105.

The user (e.g., doctor, physician, surgeon, nurse, or other health care provider, etc.) can select the tasks 495, view the tasks 495, and/or sign off on the tasks 495 such as by marking one or more tasks 495 as completed. The tasks 495 can also be reassigned to a different health care provider. Once marked as reassigned, the EMR access device 150 can transmit a signal to the middle tier application 205 and/or to the EMR database 140. Moreover, new tasks 495 can be generated from the EMR access device 150. The new tasks 495 can also be marked as completed, reassigned, transmitted to the EMR database 140, and the like.

Figure 5:
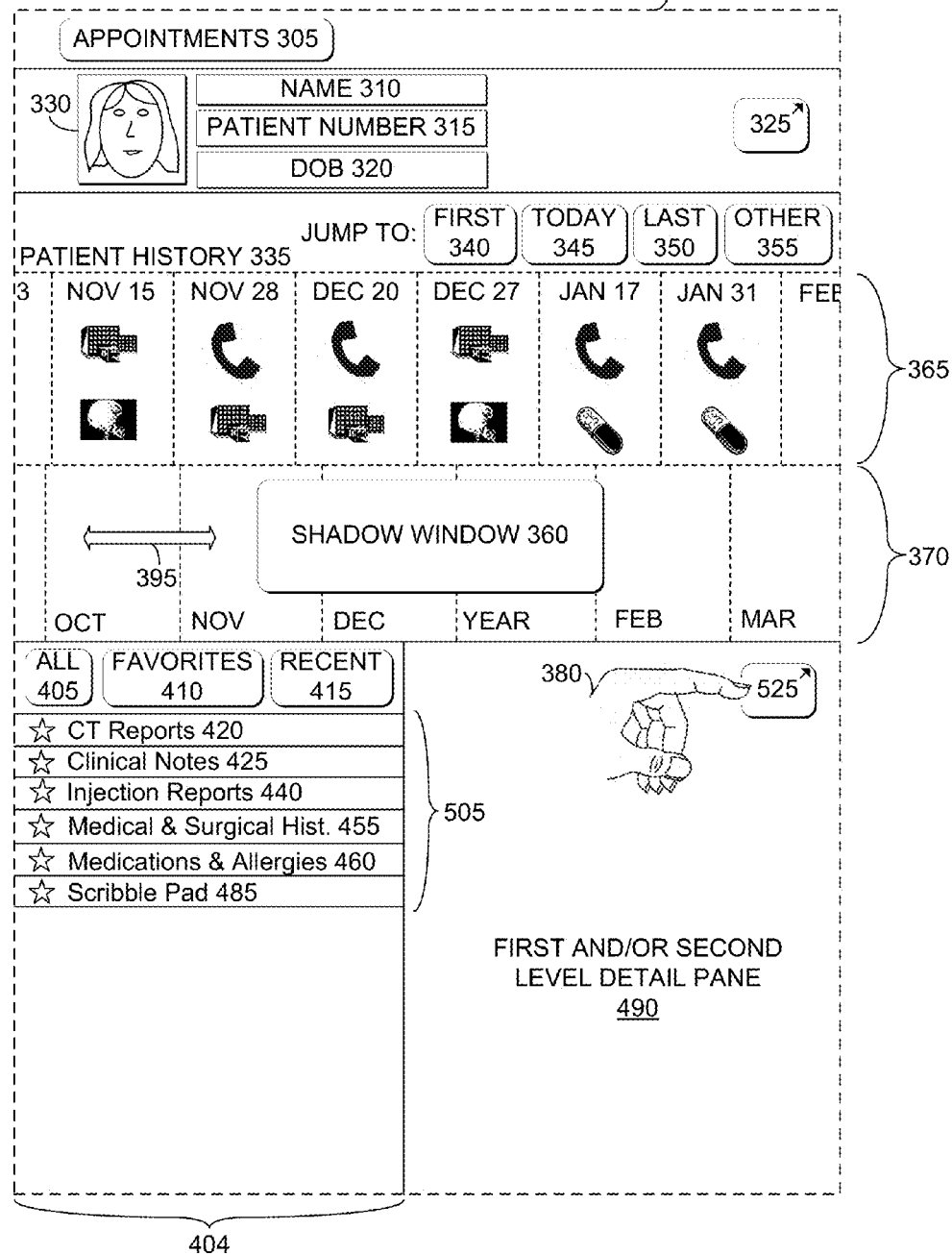
FIG. 5 illustrates the touch-sensitive user interface in yet another example mode for accessing and presenting EMR information according to some embodiments of the present invention.

FIG. 5 illustrates the list of categories 404 including only the favorite 505 categories. In this fashion, only the categories that have particular importance to a user are displayed, which provides a more intuitive and simple way to access and display the medical information.

Referring now to FIGS. 4 and 5, the EMR access device can be configured to receive a touch selection of a "favorites" 410 button or icon corresponding to the subset 505 of the list of categories. The EMR access device can further detect a preference for displaying only the favorites 505 from the list of categories 404, and display only the subset 505 corresponding to the selection of the favorites icon 410 in the itemized list of categories 404.

Furthermore, the EMR access device can be configured to receive a touch selection of an "all" button or icon 405 corresponding to all of the categories in the list of categories 404. In other words, the EMR access device can detect a preference for displaying all of the categories in the itemized list, and in response, can display all of the categories. Moreover, the EMR access device can be configured to receive a touch selection of a "recent" button or icon 415 corresponding to the most recently displayed categories in the itemized list of categories 404.

As mentioned above, each item in the list 404 corresponds to a category of medical information associated with the medical patient. The EMR access device can detect a touch selection for one or more of the categories in the list 404 so that more detailed information about the one or more categories of medical information can be displayed. A first level of detail about the selected category can be displayed in the detail pane 490 of the user interface 115. In response to a touch selection of button or icon 525, a second level of detail about the selected category can be displayed in a second detail pane 690 of FIG. 6.

Reference is now made to FIGS. 4, 5, and 6. When a user wants to know more information about a particular category of medical information associated with the patient 330, different items within the list of categories 404 can be selected so that a higher level of detail can be presented in one of the detail panes. The detail pane 490 can display a first level of detail about a selected category. The detail pane 490 can also display a second level of detail, more detailed than the first level.

Similarly, the expanded detail pane 690 (of FIG. 6) can display a second level of detail about the selected category, more detailed than the first level. In addition, the expanded detail pane 690 can display a third level of detail about the selected category, more detailed than both the first and second levels of detail. In this manner, different levels of detail about a category of medical information is accessible within a few or less touches of the touch-sensitive display 110.

For instance, if a touch selection for the clinical notes 425 is received, the EMR access device can cause a list of notes organized by date as a first level of detail displayed in the detail pane 490. If the user desires to see the contents of a note for a given date, then the user can select one of the individual items in the list of notes within the detail pane 490, which can cause the contents of the note for the given date to be shown in the detail pane 690, thereby providing a second more detailed level of information in the detail pane 690.

In some embodiments, the contents of the note can be displayed in the detail pane 490, thereby providing the second more detailed level of information in the detail pane 490. In some embodiments, a third level of detailed information about the selected clinical note 425 can be displayed in the detail pane 690. In some embodiments, the detail pane 490 can be expanded into the detail pane 690 using button or icon 525. It should be understood that different levels of detail of different categories (e.g., 420, 425, 440, 455, 460, 485, and/or 495) can be navigated in the same or a similar fashion. When the user is finished viewing the detailed information in detail pane 690, the user can touch the "done" button or icon 605 in order to exit the detail pane 690.

Figure 7:
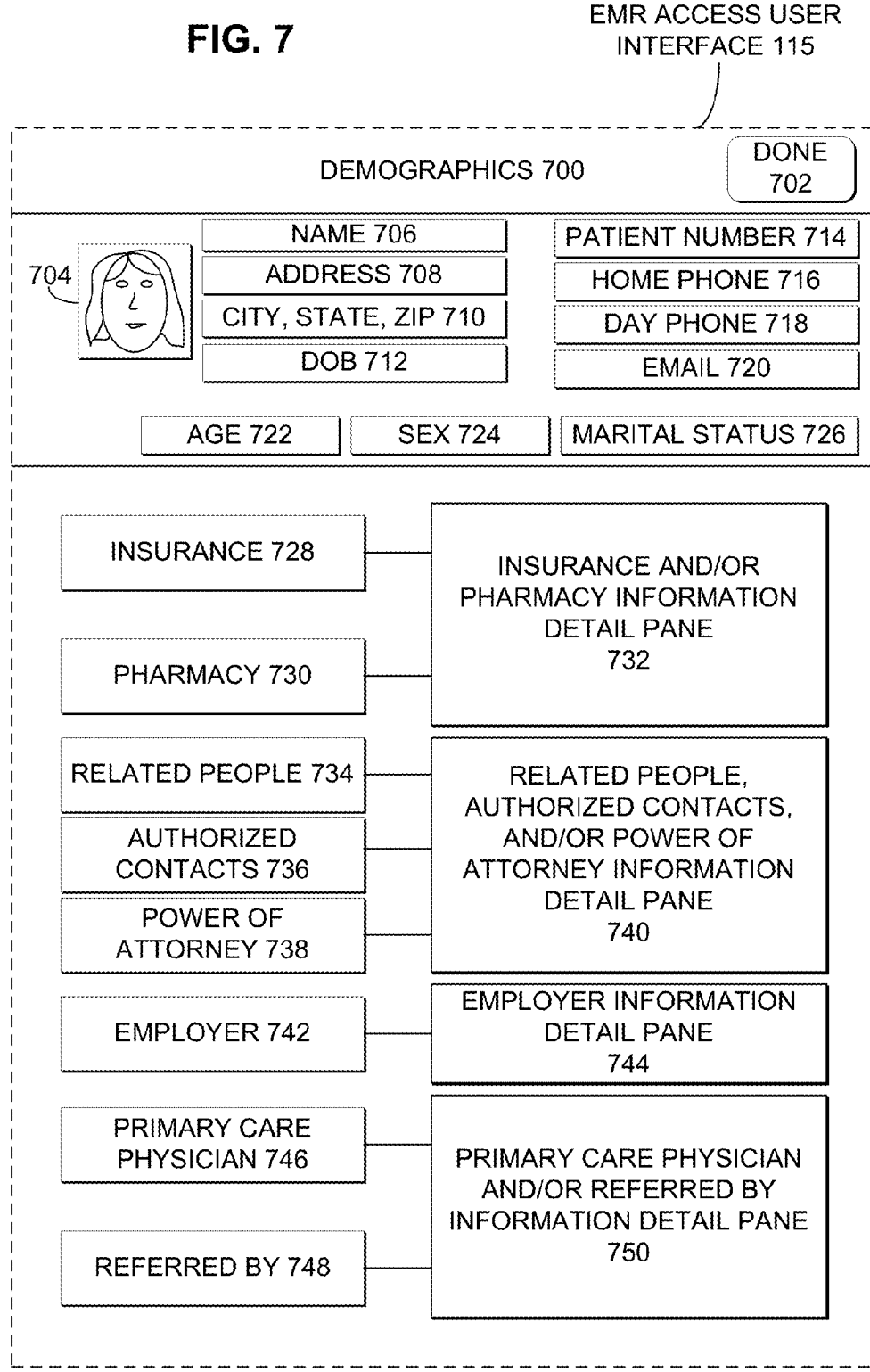
FIG. 7 illustrates the touch-sensitive user interface in another example mode for accessing and presenting EMR information according to some embodiments of the present invention.

FIG. 7 illustrates the touch-sensitive user interface 115 in another example mode for accessing and presenting EMR information according to some embodiments of the present invention. An expansion button or icon 325 (of FIG. 3) can be located in the patient information section 332, which when touched by a user of the EMR access device, expands the patient information section 332 into a patient demographics detail screen 700.

The demographics detail screen 700 can include, for example, an image of the patient 704, the patient's name 706, an identification number 714 for the patient, the patient's address 708, the patient's home phone number 716, the patient's city, state and zip code 710, the patient's day phone number 718, the patient's date of birth 712, the patient's email address 720, the patient's age 722, the patient's sex or gender 724, and/or the patient's marital status 726, or any combination thereof.

The demographics detail screen 700 can also include an indicator of the patient's insurance 728 and/or preferred pharmacy 730. An insurance and/or pharmacy information detail pane 732 provides a location in which the user can enter and/or display more detailed information about the patient's insurance 728 and/or pharmacy 730.

The demographics detail screen 700 can also include an indicator of related people 734, authorized contacts 736, and/or power of attorney 738. A related people, authorized contacts, and/or power of attorney information detail pane 740 provides a location in which the user can enter and/or display more detailed information about the patient's related people 734, authorized contacts 736, and/or power of attorney 738.

The demographics detail screen 700 can also include an indicator of the patient's employer 742. An employer information detail pane 744 provides a location in which the user can enter and/or display more detailed information about the patient's employer 742.

The demographics detail screen 700 can also include an indicator of the patient's primary care physician 746 and/or "referred by" information 748. A primary care and/or "referred by" information detail pane 750 provides a location in which the user can enter and/or display more detailed information about the patient's primary care physician 746 and/or "referred by" information 748. When the user is finished viewing the patient's demographic information, the done button or icon 702 can be touched and the demographic window 700 is closed.

FIG. 8 illustrates the touch-sensitive user interface 115 in another example mode for accessing and presenting EMR information according to some embodiments of the present invention. When the user selects the scribble pad 485 from the list of categories 404, a scribble pad 800 is displayed on the touch-sensitive display 110. Background medical information can be displayed on the scribble pad 800, including for example, a title indicating the topic such as Knee 806. The title and background information can be related to a body part, a test result, a medical chart, a diagnostics image, and so forth. Additional information 808 related to the title can indicate whether, for example, the knee is a left or right knee.

A "history of present illness" or HPI section can include background choices such as onset, context, severity, quality, and the like. Other medical indicators such as achey, throbbing, burning, swelling, and the like can be automatically provided as background information on the scribble pad 800. A user can then draw on the scribble pad 800 using their finger or a suitable tool such as a stylus. For example, a circle 810 could be drawn around a portion of the background information. Numbers or letters such as 810 can be added to enhance the information. Lines (e.g., 810) can be drawn to indicate certain symptoms are present or not present, etc.

The scribble pad 800 can include an "EXAM" section including various additional information. For instance, an image, such as the image 814 of a knee, can be automatically provided as part of the background information. The user can add lines next to or over the image 814 such as lines 812 to emphasize to the patient a particular area of interest or a particular issue, or to otherwise make a record for use by the doctor. In addition, a photograph 397 of a body part of a patient can be displayed. The user can add lines next to or over the photograph 397 to emphasize to the patient a particular area of interest or a particular issue, or to otherwise make a record for use by the doctor. The photograph 397 can be expanded or reduced in size.

A "PLAN" section can include various treatment or diagnostics options provided as background information in the scribble pad 800. The user can cross out one or more of the options or emphasize another by drawing circles, crosses, underlining, and so forth.

It should be understood that the HPI, EXAM, and PLAN sections and associated background information are but a few examples. Other background medical related information can be displayed on the scribble pad 800, over which the user can draw lines, shapes, letters, circles, crosses, and so forth, to de-emphasis and/or emphasis different portions of the supplied background information. In other words, the supplied background information provides a template upon which the user can supply additional information.

In some embodiments, the scribble pad 800 is blank, or in other words, does not include the background information, and can be drawn on from a blank starting configuration. In some embodiments, the scribble pad 800 can have any customized background. For example, a background can be customized for a hand, a heart for cardiology, an eye for ophthalmology, or some other broader or narrower medical category.

Drawing tools 816 can be used to change the color of lines, shapes, letters, circles, crosses, and so forth, or to select an eraser to erase some or all of these. The scribble pad 800 can include a line width slider scale 818. The width of the lines can be adjusted by touching the knob 820 and sliding the knob 820 to the left or to the right to change the line width. For instance, sliding the knob 820 to the right on the line width slider scale 818 can make a wider line, while sliding the knob 820 to the left on the line width slider scale 818 can make a thinner line.

The lines, shapes, letters, circles, crosses, and so forth added by the user to the scribble pad 800 can be temporarily stored as a file on a local storage device 130. The user can close the scribble pad 800 by selecting the button or icon 804, which can cause the information to be saved. After closing the scribble pad 800, the file can be sent to the middle-tier application 205 (of FIG. 2) and/or the EMR database 140 for permanent storage. Subsequently, when the scribble pad 800 for this patent is re-opened, the lines, shapes, and so forth that were added by the user will be recalled and displayed along with the associated background information. By clicking the cancel button or icon 802, the user can exit the scribble pad 800 without saving the changes.

Other information can also be transmitted to the middle-tier application 205 (of FIG. 2) and/or the EMR database 140 for permanent storage. For instance, changes made to information associated with one or more of the other categories 404 can be sent for more permanent storage. Such information can include medication and test ordering information, form completion information, and/or encounter documentation. It should be understood that while the EMR access device 105 is primarily a reader of EMR information, such "access" as described herein includes transmitting changes or other information to the middle-tier application 205 (of FIG. 2) and/or the EMR database 140 for more permanent storage and later recall.

FIG. 9 illustrates a flow diagram 900 including techniques for reading and displaying EMR information in a touch-sensitive sliding timeline, according to example embodiments of the invention. The technique begins at 905 where EMR information is read from one or more EMRs by an EMR access device. The one or more EMRs can be initially located, for example, in a middle-tier application (e.g., 205) and/or an EMR database (e.g., 140). At 910, a first portion of the EMR information can be chronologically displayed on a touch-sensitive sliding timeline.

A determination is made at 915 whether a finger swipe gesture is detected by the EMR access device. If YES, the flow proceeds to 920, and the sliding timeline is scrolled so that a second portion of the EMR information is displayed in chronological order on the touch-sensitive sliding timeline. The second portion of the EMR information can be entirely different from the first portion. Alternatively, the second portion of EMR information can overlap with or otherwise contain information from the first portion. If no finger swipe gesture is detected at 915, the flow returns to 910 for further processing.

Figure 10:
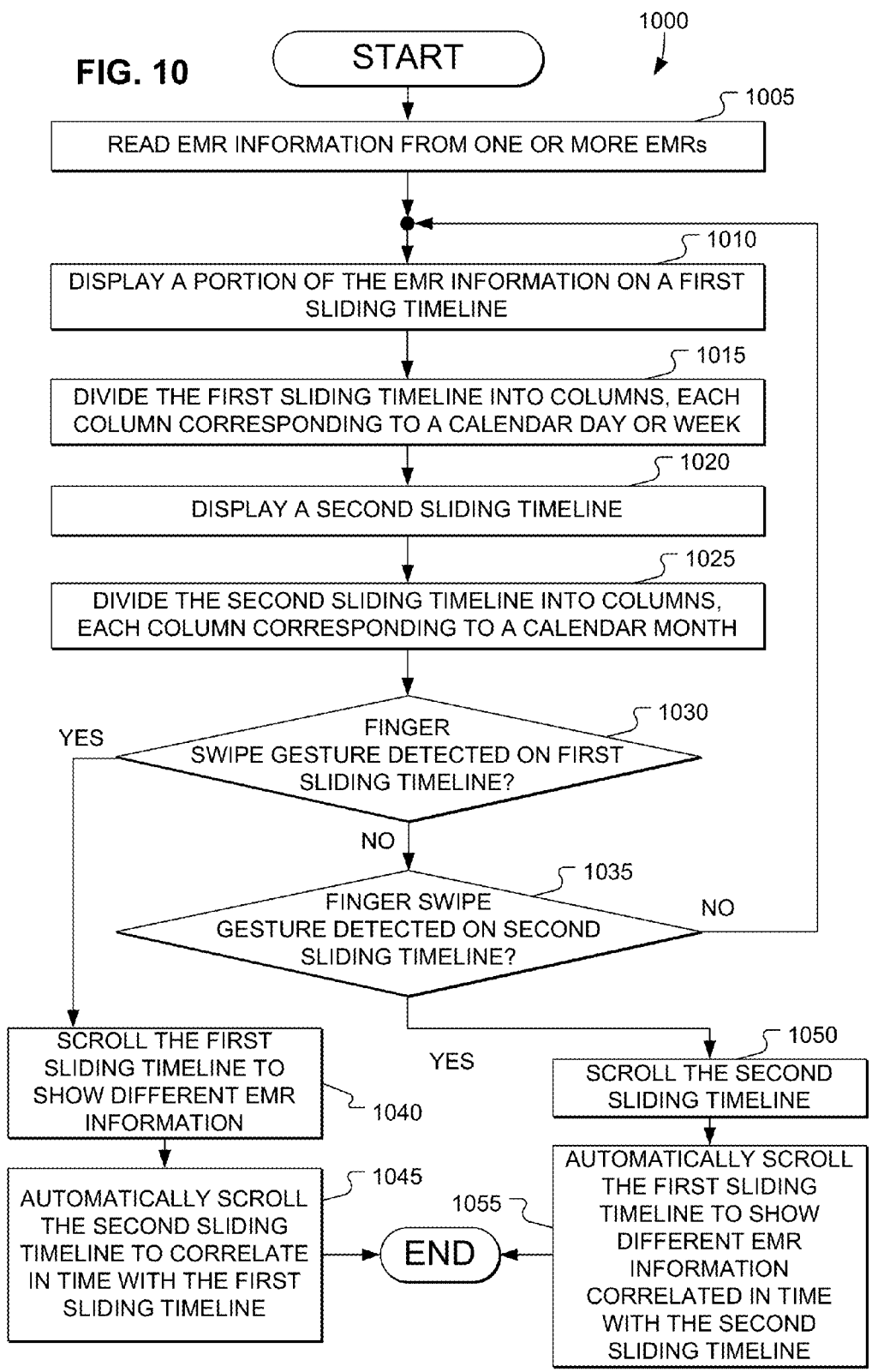
FIG. 10 illustrates a flow diagram including techniques for reading and displaying EMR information in dual touch-sensitive sliding timelines, according to example embodiments of the invention.

FIG. 10 illustrates a flow diagram 1000 including techniques for reading and displaying EMR information in dual touch-sensitive sliding timelines, according to example embodiments of the invention. The technique begins at 1005 where EMR information is read from one or more EMRs by an EMR access device. The one or more EMRs can be initially located, for example, in a middle-tier application (e.g., 205) and/or an EMR database (e.g., 140).

At 1010, a portion of the EMR information can be displayed on a first sliding timeline. At 1015, the first sliding timeline is divided into columns, each column corresponding to a calendar day or a calendar week. At 1020, a second sliding timeline is displayed. The second sliding timeline is divided into columns at 1025, each column corresponding to a calendar month. A determination is made at 1030 whether a finger swipe gesture is detected on the first sliding timeline. If YES, the flow proceeds to 1040 and the first sliding timeline is scrolled so that different EMR information is displayed in the first sliding timeline. In addition, at 1045, the second sliding timeline is automatically scrolled to correlate in time with the first sliding timeline.

If the finger swipe gesture is not detected at 1030, the flow proceeds to 1035 and a determination is made whether a finger swipe gesture is detected on the second sliding timeline. If YES, then the flow proceeds to 1050 and the second timeline is scrolled in response to the finger swipe gesture. In addition, at 1055, the first sliding timeline is automatically scrolled to show different EMR information correlated in time with the second sliding timeline. Otherwise, if the finger swipe gesture is not detected at 1035, the flow returns to 1010 for further processing.

It should be understood that the determinations at 1030 and 1035 need not occur in that order, but rather, these determinations can be made at different times. It will also be understood that the steps described in these techniques need not necessarily occur in the order as illustrated.

Although the foregoing discussion has focused on particular embodiments, other configurations are contemplated. In particular, even though expressions such as "according to an embodiment of the invention" or the like are used herein, these phrases are meant to generally reference embodiment possibilities, and are not intended to limit the invention to particular embodiment configurations. As used herein, these terms can reference the same or different embodiments that are combinable into other embodiments.

The following discussion is intended to provide a brief, general description of a suitable machine or machines in which certain aspects of the invention can be implemented. Typically, the machine or machines include a system bus to which is attached processors, memory, e.g., random access memory (RAM), read-only memory (ROM), or other state preserving medium, storage devices, a video interface, and input/output interface ports. The machine or machines can be controlled, at least in part, by input from conventional input devices, such as keyboards, mice, etc., as well as by directives received from another machine, interaction with a virtual reality (VR) environment, biometric feedback, or other input signal. As used herein, the term "machine" is intended to broadly encompass a single machine, a virtual machine, or a system of communicatively coupled machines, virtual machines, or devices operating together. Exemplary machines include computing devices such as personal computers, workstations, servers, portable computers, handheld devices, telephones, tablets, etc., as well as transportation devices, such as private or public transportation, e.g., automobiles, trains, cabs, etc.

The machine or machines can include embedded controllers, such as programmable or non-programmable logic devices or arrays, Application Specific Integrated Circuits (ASICs), embedded computers, smart cards, and the like. The machine or machines can utilize one or more connections to one or more remote machines, such as through a network interface, modem, or other communicative coupling. Machines can be interconnected by way of a physical and/or logical network, such as an intranet, the Internet, local area networks, wide area networks, etc. One skilled in the art will appreciated that network communication can utilize various wired and/or wireless short range or long range carriers and protocols, including radio frequency (RF), satellite, microwave, Institute of Electrical and Electronics Engineers (IEEE) 545.11, Bluetooth®, optical, infrared, cable, laser, etc.

Embodiments of the invention can be described by reference to or in conjunction with associated data including functions, procedures, data structures, application programs, etc. which when accessed by a machine results in the machine performing tasks or defining abstract data types or low-level hardware contexts. Associated data can be stored in, for example, the volatile and/or non-volatile memory, e.g., RAM, ROM, etc., or in other storage devices and their associated storage media, including hard-drives, floppy-disks, optical storage, tapes, flash memory, memory sticks, digital video disks, biological storage, etc. Associated data can be delivered over transmission environments, including the physical and/or logical network, in the form of packets, serial data, parallel data, propagated signals, etc., and can be used in a compressed or encrypted format. Associated data can be used in a distributed environment, and stored locally and/or remotely for machine access.

Other similar or non-similar modifications can be made without deviating from the intended scope of the invention. Accordingly, the invention is not limited except as by the appended claims.

The invention claimed is:

1. A method for accessing, processing, and presenting electronic medical record information on a touch-sensitive display, the method comprising:
   accessing one or more electronic medical records from an electronic medical record database;
   reading electronic medical record information from the one or more electronic medical records;
   locating a first portion of the electronic medical record information;
   displaying the first portion of the electronic medical record information in chronological order on a first touch-sensitive sliding timeline;
   locating a second portion of the electronic medical record information;
   scrolling the first touch-sensitive sliding timeline in response to detecting a first finger swipe gesture so that the second portion of the electronic medical record information is displayed in chronological order on the first touch-sensitive sliding timeline;
   providing a second touch-sensitive sliding timeline proximate to the first touch-sensitive sliding timeline;
   locating a third portion of the electronic medical record information;
   scrolling the second touch-sensitive sliding timeline in response to detecting a second finger swipe gesture within boundaries of the second touch-sensitive sliding timeline;
   scrolling the first touch-sensitive sliding timeline to correlate in time with the second touch-sensitive sliding timeline in response to detecting the second finger swipe gesture relative to the second touch-sensitive sliding timeline; and
   scrolling the second touch-sensitive sliding timeline to correlate in time with the first touch-sensitive sliding timeline in response to detecting the first finger swipe gesture relative to the first touch sensitive sliding timeline.

2. The method of claim 1, further comprising:
   dividing the first touch-sensitive sliding timeline into a first plurality of columns;
   associating each of the first plurality of columns with one day;
   wherein displaying the first portion includes displaying one or more first medical event indicators representing medical events having occurred during the one day within an associated column from among the first plurality of columns;
   dividing the second touch-sensitive sliding timeline into a second plurality of columns;
   associating each of the second plurality of columns with one month; and
   displaying, within an associated column from among the second plurality of columns, the third portion of the electronic medical record information as one or more second medical event indicators representing days within the one month in which a medical event occurred.

3. The method of claim 2, further comprising:
   displaying medical test results in a test results section that is proximate to at least one of the first or second touch-sensitive sliding timelines, wherein the medical test results are correlated in time to the one or more first medical event indicators,
   wherein displaying the one or more first medical event indicators includes displaying one or more icons in each of the plurality of columns, wherein each of the one or more icons represents a medical event.

4. The method of claim 3, wherein the medical event corresponds to at least one of a telephone call, an office visit, an oral medication related event, an intravenous or injection medication related event, and a medical diagnostics related event, the method further comprising:
   detecting a touch selection of an icon representing the telephone call on the touch-sensitive display;
   displaying information about the telephone call in a detail pane;
   detecting a touch selection of an icon representing the office visit on the touch-sensitive display;
   displaying information about the office visit in the detail pane;
   detecting a touch selection of an icon representing the oral medication related event on the touch-sensitive display;
   displaying information about the oral medication related event in the detail pane;
   detecting a touch selection of an icon representing the intravenous or injection medication related event on the touch-sensitive display;
   displaying information about the intravenous medication related event in the detail pane;
   detecting a touch selection of an icon representing the medical diagnostics related event on the touch-sensitive display; and
   displaying information about the medical diagnostics related event in the detail pane.

5. The method of claim 2, further comprising:
   detecting a touch selection of a "first" event preference on the touch-sensitive display;
   automatically scrolling the first sliding timeline to the first calendar day column from among the first plurality of columns responsive to detecting the "first" event preference selection;
   detecting a touch selection of a "last" event preference on the touch-sensitive display;
   automatically scrolling the first sliding timeline to the last calendar day column from among the first plurality of columns responsive to detecting the "last" event preference selection;
   detecting a touch selection of a "today" event preference on the touch-sensitive display; and
   automatically scrolling the first sliding timeline to the calendar day column from among the first plurality of columns corresponding to the present calendar day responsive to detecting the "today" event preference selection.

6. The method of claim 1, further comprising:
   detecting an inward finger pinch gesture on the touch-sensitive display on or near the first touch-sensitive sliding timeline; and
   expanding the resolution of the first touch-sensitive sliding timeline from increments of days to increments of weeks responsive to the finger pinch gesture.

7. The method of claim 1, further comprising:
   detecting an outward finger pinch gesture on the touch-sensitive display on or near the first touch-sensitive sliding timeline; and
   collapsing the resolution of the sliding timeline from increments of weeks to increments of days responsive to the outward finger pinch gesture.

8. The method of claim 1, wherein:
   displaying the third portion of the medical record information includes displaying one or more icons on the second touch-sensitive sliding timeline representing a day within at least one calendar month in which a medical event occurred.

9. The method of claim 1, further comprising:
displaying a list of medical categories associated with a medical patient;
receiving a touch selection of favorites corresponding to a subset of the list of medical categories;
detecting a preference for displaying only the favorites from the list of medical categories; and
displaying only the subset corresponding to the selection of favorites in the list of medical categories.

10. The method of claim 9, wherein each item in the list corresponds to a category of medical information associated with the medical patient, the method further comprising:
detecting a touch selection of one of the categories in the subset of the list of categories corresponding to one category of medical information;
displaying a first level of detail in a first detail pane about the selected category of medical information; and
displaying a second level of detail in a second detail pane about the selected category of medical information.

11. The method of claim 9, further comprising:
capturing a photograph of a body part of the medical patient; and
storing the photograph of the body part in the electronic medical records database.

12. The method of claim 9, wherein one item in the list of categories corresponds to a scribble pad, the method further comprising:
detecting a touch selection of the scribble pad item;
displaying a scribble pad on the touch-sensitive display;
displaying medical information on the scribble pad;
receiving touch signals on areas of the scribble pad;
drawing lines or shapes corresponding to the areas of the scribble pad associated with the received touch signals; and
temporarily storing the lines and the medical information displayed on the scribble pad as a file on a local storage device; and
after closing the scribble pad, sending the file to the electronic medical records database for permanent storage.

13. The method of claim 11, further comprising:
displaying a line width slider scale; and
adjusting the line width of the lines drawn based on the touch signals responsive to an adjustment of the line width slider scale.

14. The method of claim 1, further comprising:
marking or signing the one or more electronic medical records as having been reviewed; and
storing the one or more marked or signed electronic medical records in the electronic medical records database.

15. The method of claim 1, further comprising:
remotely sensing a particular medical patient within a vicinity of the touch-sensitive display; and
automatically opening and displaying the electronic medical record information for the particular medical patient on the touch-sensitive display.

16. A system for accessing, processing, and presenting electronic medical record information, the system comprising:
an electronic medical records database including a plurality of electronic medical records; and
one or more portable electronic medical record access devices configured to communicate with the electronic medical records database and extract electronic medical record information from the electronic medical records database, wherein the one or more portable electronic medical record access devices include a controller and a touch-sensitive display configured to display the electronic medical record information and receive touch selections associated with the displayed information, wherein the controller is further configured to:
locate a first portion of the electronic medical record information;
display the first portion of the electronic medical record information in chronological order on a first touch-sensitive sliding timeline;
locate a second portion of the electronic medical record information;
scroll the first touch-sensitive sliding timeline in response to detecting a first finger swipe gesture so that the second portion of the electronic medical record information is displayed in chronological order on the first touch-sensitive sliding timeline;
provide a second touch-sensitive sliding timeline proximate to the first touch-sensitive sliding timeline;
locate a third portion of the electronic medical record information;
scroll the second touch-sensitive sliding timeline in response to detecting a second finger swipe gesture within boundaries of the second touch-sensitive sliding timeline;
scroll the first touch-sensitive sliding timeline to correlate in time with the second touch-sensitive sliding timeline in response to detecting the second finger swipe gesture relative to the second touch-sensitive sliding timeline; and
scroll the second touch-sensitive sliding timeline to correlate in time with the first touch-sensitive sliding timeline in response to detecting the first finger swipe gesture relative to the first touch sensitive sliding timeline.

17. The system of claim 16, wherein the controller is further configured to:
divide the second touch-sensitive sliding timeline into a second plurality of columns;
associate each of the second plurality of columns with one month;
display one or more first medical event indicators representing medical events having occurred during the one day within an associated column from among the first plurality of columns;
divide the first touch-sensitive sliding timeline into a first plurality of columns;
associate each of the first plurality of columns with one day; and
display, within an associated column from among the second plurality of columns, the third portion of the electronic medical record information as one or more second medical event indicators representing days within the one month in which a medical event occurred.

18. The system of claim 16, wherein the one or more portable electronic medical record access devices include:
an input output interface configured to wirelessly communicate with the electronic medical records database; and
a local storage configured to store the electronic medical record information received from the electronic medical records database.

19. The system of claim 16, wherein:
the second touch-sensitive sliding timeline includes a shadow window correlating with an amount of time showing in the first touch-sensitive sliding timeline.

20. A non-transitory computer-readable medium including instructions executable by a processor, the instructions comprising:
instructions for accessing one or more electronic medical records from an electronic medical record database;
instructions for reading electronic medical record information from the one or more electronic medical records;
instructions for locating a first portion of the electronic medical record information;
instructions for displaying the first portion of the electronic medical record information in chronological order on a first touch-sensitive sliding timeline;
instructions for locating a second portion of the electronic medical record information;
instructions for scrolling the first touch-sensitive sliding timeline in response to detecting a first finger swipe gesture so that the second portion of the electronic medical record information is displayed in chronological order on the first touch-sensitive sliding timeline;
instructions for providing a second touch-sensitive sliding timeline proximate to the first touch-sensitive sliding timeline;
instructions for locating a third portion of the electronic medical record information;
instructions for scrolling the second touch-sensitive sliding timeline in response to detecting a second finger swipe gesture within boundaries of the second touch-sensitive sliding timeline;
instructions for scrolling the first touch-sensitive sliding timeline to correlate in time with the second touch-sensitive sliding timeline in response to detecting the second finger swipe gesture relative to the second touch-sensitive sliding timeline; and
instructions for scrolling the second touch-sensitive sliding timeline to correlate in time with the first touch-sensitive sliding timeline in response to detecting the first finger swipe gesture relative to the first touch sensitive sliding timeline.

* * * * *